(12) United States Patent
Yamada et al.

(10) Patent No.: US 9,145,382 B2
(45) Date of Patent: Sep. 29, 2015

(54) ORGANIC COMPOUND AND ELECTROCHROMIC DEVICE USING THE SAME

(71) Applicant: CANON KABUSHIKI KAISHA, Tokyo (JP)

(72) Inventors: Kenji Yamada, Yokohama (JP); Jun Yamamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/614,660

(22) Filed: Feb. 5, 2015

(65) Prior Publication Data

US 2015/0227016 A1     Aug. 13, 2015

(30) Foreign Application Priority Data

Feb. 12, 2014  (JP) ................ 2014-024330
Feb. 2, 2015   (JP) ................ 2015-018345

(51) Int. Cl.
*C07D 333/16*     (2006.01)

(52) U.S. Cl.
CPC .................... *C07D 333/16* (2013.01)

(58) Field of Classification Search
CPC ..................................................... C07D 333/16
USPC ........................................................ 549/78
See application file for complete search history.

(56) References Cited

U.S. PATENT DOCUMENTS

| | | |
|---|---|---|
| 4,902,108 A | 2/1990 | Byker |
| 5,128,799 A | 7/1992 | Byker |
| 5,290,930 A | 3/1994 | Byker |
| 5,481,395 A | 1/1996 | Byker |
| 5,751,467 A | 5/1998 | Byker |
| 5,801,873 A | 9/1998 | Byker |
| 6,016,215 A | 1/2000 | Byker |
| 6,211,994 B1 | 4/2001 | Byker |
| 6,351,328 B1 | 2/2002 | Byker |
| 2015/0031894 A1 | 1/2015 | Yamada et al. |

FOREIGN PATENT DOCUMENTS

| | | |
|---|---|---|
| JP | 9-120088 A | 5/1997 |
| WO | 2013/099523 A1 | 7/2013 |

OTHER PUBLICATIONS

J. Guay et al., "Chain-Length Dependence of Electrochemical and Electronic Properties of Neutral and Oxidized Soluble α, α-Coupled Thiophene Oligomers," 4(5) Chem. Mater. 1097-1105 (Sep. 1992).
Keith J. Stone et al., "Heterocyclic Aromatic Non-Kekule Molecules. Synthesis and Solution-Phase Chemistry of the Singlet Biradicals 3,4-Dimethylenefuran and 3,4-Dimethylenethiophene," 111(10) J. Am. Chem. Soc. 3659-3671 (May 1989).

*Primary Examiner* — Taofiq A Solola
(74) *Attorney, Agent, or Firm* — Fitzpatrick, Cella, Harper & Scinto

(57) ABSTRACT

The present invention provides an organic compound represented by the following general formula [1], the organic compound having high solubility in a polar solvent used in an EC device, high transparency in the bleached state and high stability against repetition of an oxidation-reduction reaction.

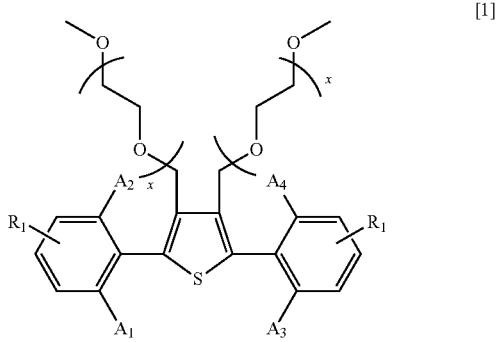

[1]

13 Claims, 7 Drawing Sheets

ORGANIC COMPOUND AND ELECTROCHROMIC DEVICE USING THE SAME

BACKGROUND OF THE INVENTION

1. Field of the Invention

The present invention relates to an electrochromic organic compound and an electrochromic device using the same.

2. Description of the Related Art

Various materials have been reported as an electrochromic (hereinafter may be abbreviated as "EC") material in which optical absorption properties (colored state and light transmittance) of a material is changed by an electrochemical oxidation-reduction reaction. A material using a metal oxide such as $WO_3$ is known as an inorganic EC material, but the material has a problem when a device having a large area is produced because a film-forming method is limited to deposition or the like.

Incidentally, conductive polymers such as polythiophene and polyaniline, organic low-molecular compounds such as viologen and oligothiophene and the like are known as an organic EC material. Here, examples of the organic low-molecular EC compounds include a viologen derivative which is a cathodic compound that is colored by reduction and an oligothiophene derivative which is an anodic compound that is colored by oxidation.

These organic low-molecular EC compounds transmit visible light in the neutral state because the compounds each have a shorter π-conjugated chain length than a conductive polymer and have absorption in an ultraviolet region. Further, these organic low-molecular EC compounds absorb visible light in the oxidized state (state of an anodic compound) or in the reduced state (state of a cathodic compound). This is because the wavelength region that absorbs light is a visible light region since the conjugated chain length of the compound in the oxidized state or the reduced state is longer than that of the compound in the neutral state.

That is, the organic low-molecular EC compound is characterized in that it is bleached in the neutral state and colored in the oxidized state or the reduced state.

Japanese Patent Application Laid-Open No. H09-120088 discloses a viologen derivative which is colored in the reduced state, and International Publication WO2013/099523 and CHAIN-LENGTH DEPENDENCE OF ELECTROCHEMICAL AND ELECTRONIC-PROPERTIES OF NEUTRAL AND OXIDIZED SOLUBLE ALPHA, ALPHA-COUPLED THIOPHENE OLIGOMERS, GUAY, J; KASAI, P; DIAZ, A et al., Chemistry of Materials, 1992, vol. 4, No. 5, pp. 1097-1105 disclose an oligothiophene derivative which is colored in the oxidized state.

Incidentally, an EC device using an organic low-molecular EC compound has high transparency in the bleached state. Examples of the EC device using an organic low-molecular EC compound that is known include a sandwiched-type device in which the EC compound is dissolved in a solvent such as propylene carbonate and the solution is sandwiched with a pair of electrodes.

In the solution-type EC device using an organic low-molecular EC compound, the organic low-molecular EC compound can be dissolved in a solvent at high concentration in order to increase the optical density (decrease transmittance) in the colored state.

However, an oligothiophene derivative disclosed in CHAIN-LENGTH DEPENDENCE OF ELECTROCHEMICAL AND ELECTRONIC-PROPERTIES OF NEUTRAL AND OXIDIZED SOLUBLE ALPHA, ALPHA-COUPLED THIOPHENE OLIGOMERS, GUAY, J; KASAI, P; DIAZ, A et al., Chemistry of Materials, 1992, vol. 4, No. 5, pp. 1097-1105 has a low solubility in a solvent, and the stability of the compound in the case of repeating an oxidation-reduction reaction is low. Further, although the thiophene derivative disclosed in International Publication WO2013/099523 has high durability against repetition of an oxidation-reduction, its solubility in a polar solvent used in an EC device is not so high.

On the other hand, although the viologen derivative (cathodic compound) described in Japanese Patent Application Laid-Open No. H09-120088 has high solubility in a polar solvent used in an EC device resulting from the molecular structure thereof, it has been a problem that the stability of the compound in the case of repeating an oxidation-reduction reaction is low.

SUMMARY OF THE INVENTION

The present invention has been made to solve the above problems, and an object of the present invention is to provide an organic compound having high solubility in a polar solvent used in an EC device, high transparency in the bleached state and high stability against repetition of an oxidation-reduction reaction.

The organic compound of the present inventions is represented by the following general formula [1].

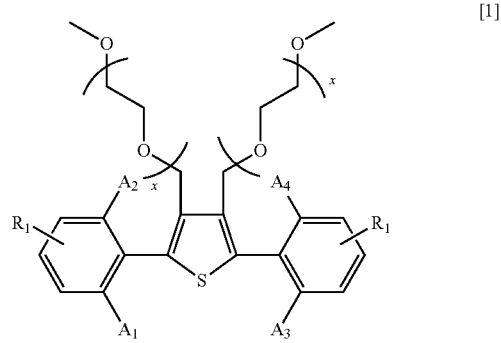

In formula [1], $A_1$ to $A_4$ each represent a substituent selected from the group consisting of a hydrogen atom, an alkyl group having 1 or more and 20 or less carbon atoms, an alkoxy group having 1 or more and 20 or less carbon atoms and an aryl group, provided that at least one of $A_1$ to $A_4$ is an alkyl group, an alkoxy group or an aryl group, wherein when any one of $A_1$ to $A_4$ is an aryl group, the aryl group may further have an alkyl group having 1 or more and 8 or less carbon atoms or an alkoxy group having 1 or more and 8 or less carbon atoms.

$R_1$ represents a hydrogen atom, a halogen atom, an alkyl group having 1 or more and 20 or less carbon atoms, an alkoxy group having 1 or more and 20 or less carbon atoms, an alkyl ester group having 1 or more and 20 or less carbon atoms, an aryl group, an optionally substituted amino group or a cyano group, wherein when $R_1$ is an aryl group, the aryl group may further have an alkyl group having 1 or more and 4 or less carbon atoms.

X is an integer of 1 to 10.

Further features of the present invention will become apparent from the following description of exemplary embodiments with reference to the attached drawings.

DESCRIPTION OF THE EMBODIMENTS

Figure 1:
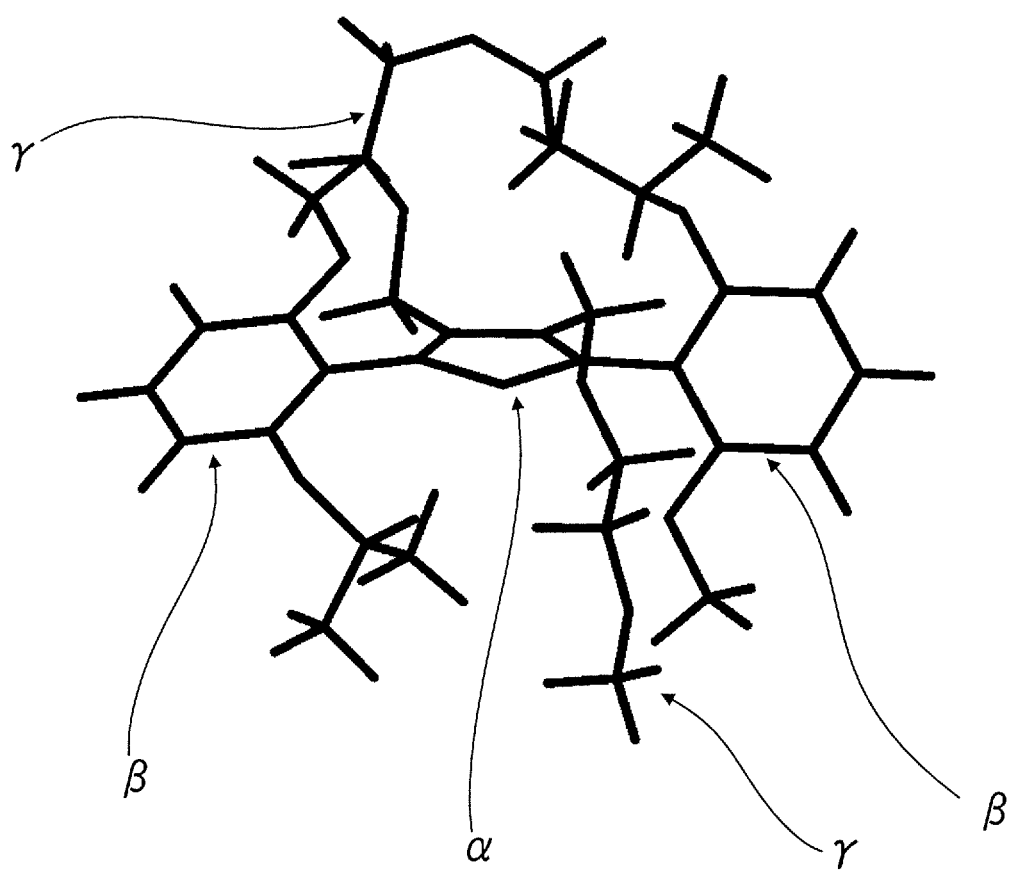
FIG. 1 shows the three-dimensional structure of a compound 2.

Preferred Embodiments of the Present Invention will now be described in detail in accordance with the accompanying drawings.

[Organic Compound]

First, the organic compound according to the present invention will be described. The organic compound of the present invention is an organic compound having electrochromic characteristics, specifically a compound represented by the following general formula [1].

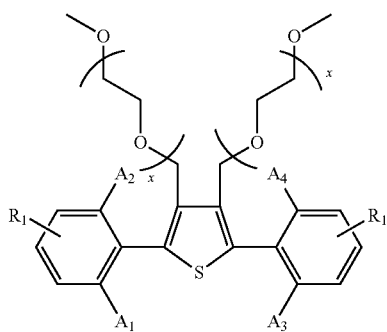

[1]

In formula [1], $A_1$ to $A_4$ each represent a substituent selected from the group consisting of a hydrogen atom, an alkyl group having 1 or more and 20 or less carbon atoms, an alkoxy group having 1 or more and 20 or less carbon atoms, an aryl group and a heterocyclic group, provided that at least one of $A_1$ to $A_4$ is an alkyl group, an alkoxy group or an aryl group. Further, in the present invention, $A_3$ can preferably be the same substituent as $A_1$, and $A_4$ can preferably be the same substituent as $A_2$.

The alkyl group represented by $A_1$ to $A_4$ may be a linear, branched or cyclic alkyl group. Preferably, the alkyl group represented by $A_1$ to $A_4$ can be an alkyl group having 1 or more and 6 or less carbon atoms.

Examples of the alkyl group represented by $A_1$ to $A_4$ include a methyl group, an ethyl group, a normal propyl group, an isopropyl group, a normal butyl group, a tertiary butyl group, a pentyl group, a hexyl group, an octyl group, a dodecyl group, a cyclohexyl group, a bicyclooctyl group and an adamanthyl group. Note that at least a part of the hydrogen atoms contained in the alkyl group may be replaced by a fluorine atom, forming, for example, a trifluoromethyl group.

The alkyl group represented by $A_1$ to $A_4$ is preferably a methyl group, an ethyl group, a normal butyl group or a hexyl group, more preferably a methyl group or an ethyl group.

The alkoxy group represented by $A_1$ to $A_4$ may be a linear, branched or cyclic alkoxy group. Preferably, the alkoxy group represented by $A_1$ to $A_4$ can be an alkoxy group having 1 or more and 8 or less carbon atoms.

Examples of the alkoxy group represented by $A_1$ to $A_4$ include a methoxy group, an ethoxy group, an isopropoxy group, a n-butoxy group, a tert-butoxy group, an ethylhexyloxy group, an octyloxy group and a benzyloxy group.

The alkoxy group represented by $A_1$ to $A_4$ is preferably a methoxy group, an ethoxy group or an isopropoxy group, more preferably a methoxy group or an isopropoxy group.

Examples of the aryl group represented by $A_1$ to $A_4$ include a phenyl group, a biphenyl group, a fluorenyl group, a naphthyl group, a fluoranthenyl group, an anthryl group, a phenanthryl group, a pyrenyl group and a perylenyl group. The aryl group represented by $A_1$ to $A_4$ is preferably a phenyl group.

Note that when any one of $A_1$ to $A_4$ is an aryl group, the aryl group may further have an alkyl group having 1 or more and 8 or less carbon atoms (preferably 1 or more and 4 or less carbon atoms), an alkoxy group having 1 or more and 8 or less carbon atoms (preferably 1 or more and 4 or less carbon atoms), an aryl group, an aralkyl group, a substituted amino group or a substituted silyl group, specifically a phenyl group, a biphenyl group, a naphthyl group, a benzyl group, a dimethylamino group, a triisopropylsilyl group or the like.

Examples of the heterocyclic group represented by $A_1$ to $A_4$ include a pyridyl group and an indolyl group. The heterocyclic group represented by $A_1$ to $A_4$ is preferably a pyridyl group.

In the present invention, at least one of $A_1$ to $A_4$ can preferably be an alkoxy group having 1 or more and 20 or less carbon atoms.

In formula [1], $R_1$ represents a hydrogen atom, a halogen atom, an alkyl group having 1 or more and 20 or less carbon atoms, an alkoxy group having 1 or more and 20 or less carbon atoms, an alkyl ester group having 1 or more and 20 or less carbon atoms, an aryl group, an optionally substituted amino group or a cyano group.

Examples of the halogen atom represented by $R_1$ include a fluorine atom.

Examples of the alkyl group represented by $R_1$ include a methyl group, an ethyl group, a normal propyl group, an isopropyl group, a normal butyl group, a tertiary butyl group, a pentyl group, a hexyl group, an octyl group, a dodecyl group, a cyclohexyl group, a bicyclooctyl group and an adamanthyl group.

Examples of the alkoxy group represented by $R_1$ include a methoxy group, an ethoxy group, an isopropoxy group, a n-butoxy group, a tert-butoxy group, an ethylhexyloxy group, an octyloxy group and a benzyloxy group.

Examples of the alkyl ester group represented by $R_1$ include a methoxycarbonyl group and an isopropoxycarbonyl group.

Examples of the aryl group represented by $R_1$ include a phenyl group, a biphenyl group, a fluorenyl group, a naphthyl group, a fluoranthenyl group, an anthryl group, a phenanthryl group, a pyrenyl group and a perylenyl group. Note that when $R_1$ is an aryl group, the aryl group may further have an alkyl group having 1 or more and 4 or less carbon atoms.

Examples of the optionally substituted amino group represented by $R_1$ include a dimethylamino group.

In formula [1], X represents the number of ethylene oxide repeating units contained in substituents at the 3-position and 4-position of the thiophene ring, specifically an integer of 1 to 10. X is preferably an integer of 1 or more and 5 or less.

[Synthetic Method of Organic Compound]

The organic compound of the present invention can be synthesized, for example, by using a scheme 1 or 2 shown below. Note that Y shown in the following scheme represents a halogen atom.

[Scheme 1]

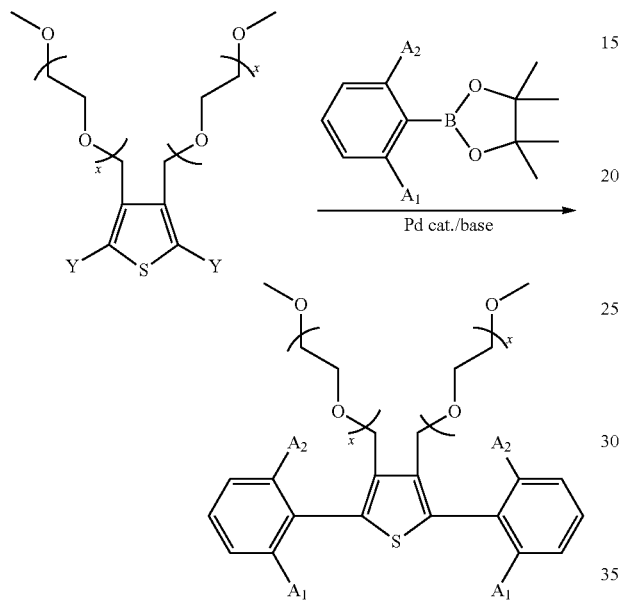

[Scheme 2]

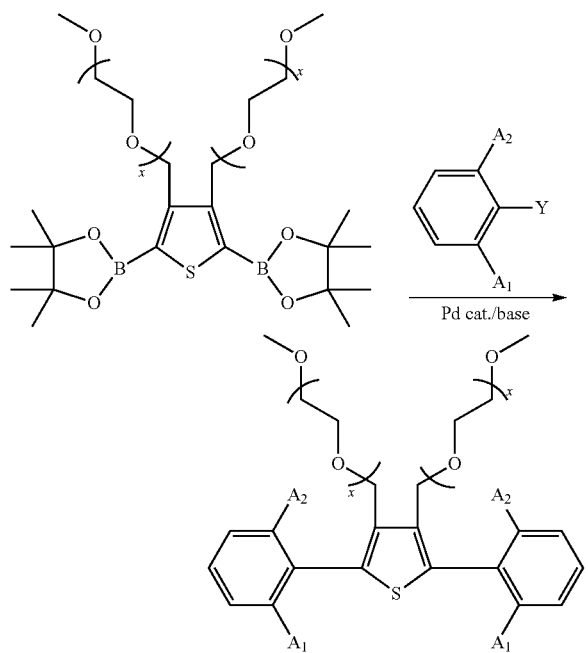

Here, the scheme 1 is a scheme with respect to the coupling reaction between a halogenated thiophene having ethylene oxide chains and a phenylboronic acid or a phenylboronic acid ester each having predetermined substituents at two ortho positions. On the other hand, the scheme 2 is a scheme with respect to the coupling reaction between a thiophene diboronic acid or a thiophene diboronic acid ester each having ethylene oxide chains and a halogenated benzene having predetermined substituents at ortho positions.

[Characteristics of Organic Compound]

Next, the characteristics of the organic compound of the present invention, particularly the characteristics based on the structure of the compound, will be described. FIG. 1 is a diagram illustrating the three-dimensional structure of a compound 2 to be described below. Note that the compound 2 is one of the organic compounds according to the present invention (illustrated compound A-1), as described below.

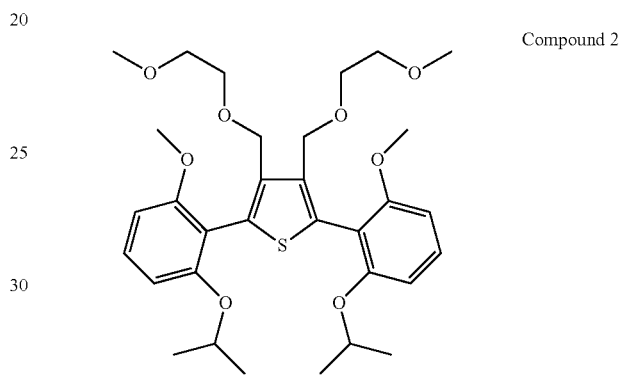

Compound 2

Note that the three-dimensional structure illustrated in FIG. 1 was obtained by performing calculation for structure optimization in a ground state using Gaussian03*Revision D.01 which is electronic state calculation software. At this time, the Density Functional Theory was employed as a quantum chemical calculation method, and B3LYP was used for the functional. In the Gaussian 03, Revision D.01, 6-31G* was used for the basis function.

*Gaussian 03, Revision D.01,

M. J. Frisch, G. W. Trucks, H. B. Schlegel, G. E. Scuseria, M. A. Robb, J. R. Cheeseman, J. A. Montgomery, Jr., T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S. Clifford, J. Cioslowski, B. B. Stefanov, G. Liu, A. Liashenko, P. Piskorz, I. Komaromi, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, C. Gonzalez, and J. A. Pople, Gaussian, Inc., Wallingford Conn., 2004.

In FIG. 1, α represents a thiophene ring; each β represents a phenyl group having an isopropoxy group and a methoxy group as terminal moieties; and each γ represents an ethylene oxide chain substituted at the 3-position and the 4-position of the thiophene ring. Note that in the following description, the thiophene ring, the phenyl group and the ethylene oxide chain as described above may be referred to as a unit α, a unit β, and a unit γ, respectively.

Here, in the thiophene ring (unit α) having electrochromic characteristics, intermolecular contact with other molecules is difficult due to the ethylene oxide chains (unit γ) and the phenyl groups (unit β) having terminal moieties ($A_1$ to $A_4$).

Therefore, when bulky substituents are provided in $A_1$ to $A_4$, since the thiophene moiety (unit α) in which radical cations are mainly produced has a clathrated molecular shape by the unit β, the thiophene moiety generates an effect in which the contact with other molecules is suppressed (the cage effect).

In the organic compound according to the present invention, the thiophene ring (unit α) having electrochromic characteristics has a short π-conjugated system as compared with a conductive polymer. Here, the short π-conjugated system means that the energy of absorbed light is high, that is, the wavelength of absorbed light by the unit α is short.

Therefore, the organic compound according to the present invention in the neutral state has light absorption in the ultraviolet region having higher energy than the visible light region, while since the compound does not have absorption in the visible light region, hence the compound has high transparency.

On the other hand, the organic compound according to the present invention in the oxidized state has light absorption in the visible light region, forming a colored state. In the case of a conductive polymer, since the polymer has light absorption in the visible light region in the neutral state, so called "remnant" is observed even in the oxidized state, the "remnant" being a phenomenon in which a portion of the polymer where electrochemical reaction is insufficient has an absorption band in the visible light region.

Meanwhile, the organic compound according to the present invention can maintain high transparency because the compound does not have an absorption band in a visible light region even when electrochemical reaction is insufficient.

Incidentally, since a compound having one thiophene ring such as the organic compound of the present invention has a short π-conjugated system as compared with a conductive polymer, the stability thereof in a radical cation state is not sufficient.

Therefore, the organic compound according to the present invention is formed into a structure having the units β and the units γ in the thiophene ring (unit α), as illustrated in FIG. 1. Having the units β and the units γ causes intermolecular contact with other molecules to be difficult, resulting in the effect that the thiophene ring which produces radical cations is protected.

The instability of radical cations is caused by recombination of radicals due to high reactivity of radicals, hydrogen abstraction from other molecules by radicals and the like. That is, the instability is caused by the reaction of radicals by the contact of radicals with other molecules. Therefore, the function of steric hindrance brought about by the unit β and the unit γ illustrated in FIG. 1 generates the effect of increasing the stability of radical cations.

Further, in the structure having the above unit α, units β, and units γ, the radical cations which are present when the compound is oxidized can be localized in the thiophene ring moiety (unit α). Therefore, since the thiophene ring moiety (unit α) is hardly attacked from the outside of the molecule by the shielding structure of sterically-hindered substituents (units β and units γ) the stability of the radical cation state of the compound will probably be significantly improved.

Therefore, the substituents ($A_1$ to $A_4$) in the unit β are preferably an alkyl group, an alkoxy group or an aryl group which serve as a steric hindrance group.

Further, since the radical cations produced in the core moiety can be stabilized by increasing the electron density of the core moiety (unit α), the substituents ($A_1$ to $A_4$) in the unit β are more preferably electron-donating substituents. An isopropoxy group, a tert-butoxy group, an ethylhexyloxy group and a benzyloxy group are particularly preferred as substituents having high electron-donating properties and large steric hindrance.

On the other hand, the organic compound of the present invention needs to have increased solubility in a polar solvent such as an electrolyte solution which is an electrochromic medium. Here, in order to have increased solubility in a polar solvent, the substituents ($A_1$ to $A_4$) in the unit β are preferably polar substituents such as an alkoxy group. Therefore, the substituents are particularly preferably an alkoxy group which functions also as a steric hindrance group, specifically an alkoxy group which is bulkier than a methoxy group.

Further, when X representing the number of repeating units of the ethylene oxide chain constituting the unit γ is increased, the length of the ethylene oxide chain is increased, showing high compatibility to a polar solvent. Thus, the solubility in a polar solvent can be increased, and the compound can be dissolved in high concentration. However, when the ethylene oxide chain is too long, the ethylene oxide chain will completely enclose the thiophene ring having electrochromic characteristics. Therefore, the contact of the thiophene ring with electrodes, that is, electrode reaction essential for electrochromic reaction, may be inhibited. Therefore, in order to satisfy both the solubility and the electrode reaction, the number of repeating units of ethylene oxide represented by X is set to 1 to 10, preferably 1 to 5.

Specific examples of the organic compound according to the present invention will be shown below. However, the organic compound according to the present invention is not limited to these examples.

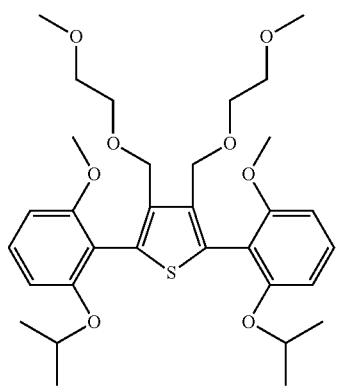

A-1

A-2
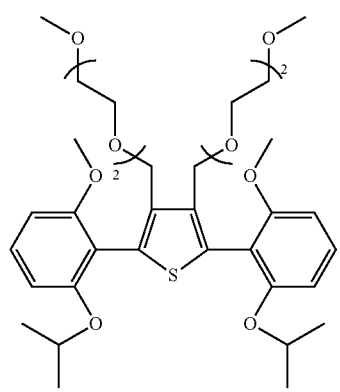
A-6
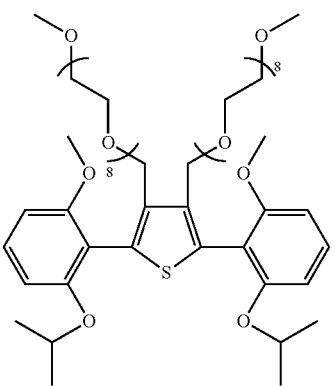
A-3
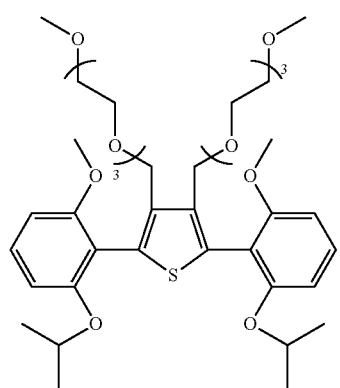
A-7
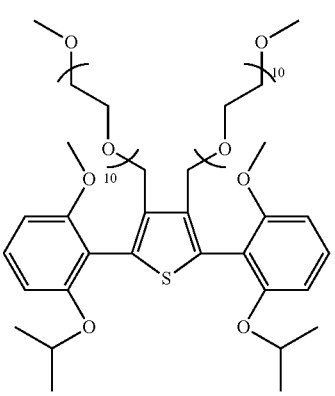
A-4
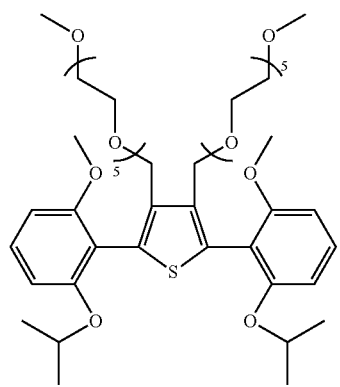
B-1
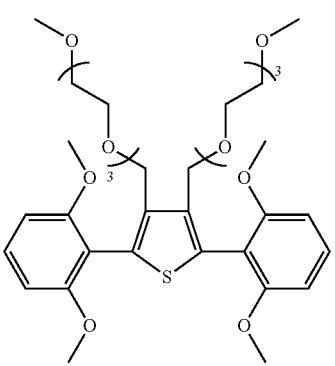
A-5
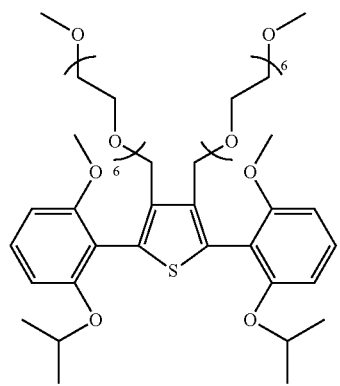
B-2
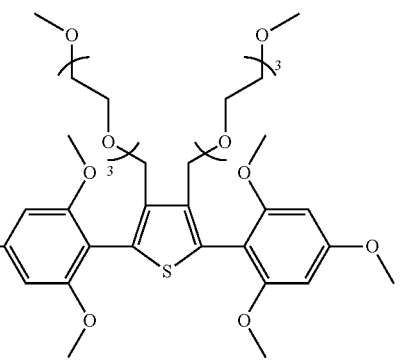

-continued
B-3
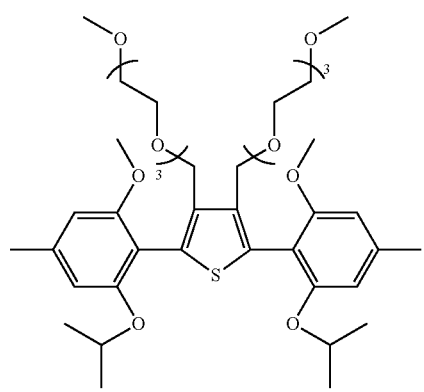
B-4
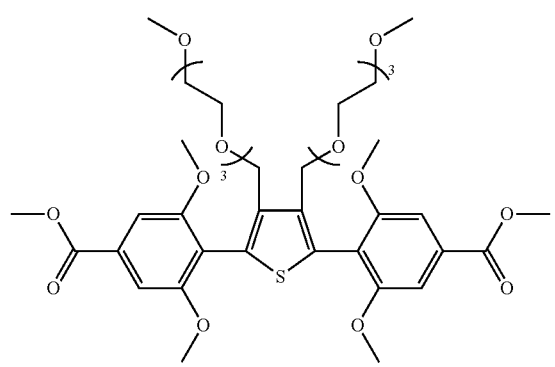
B-5
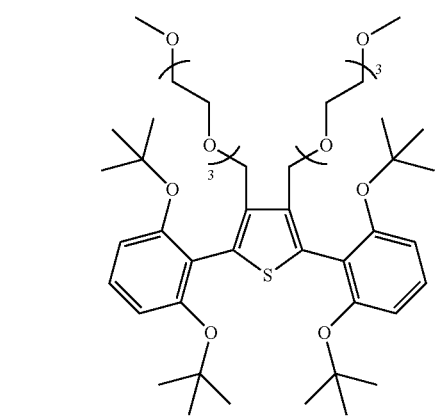
B-6
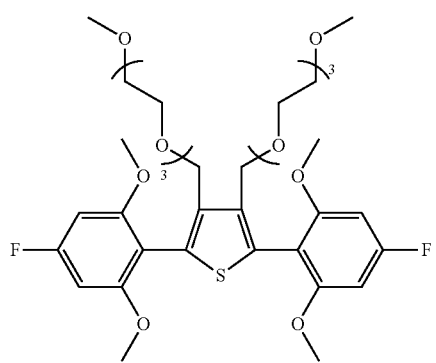
-continued
B-7
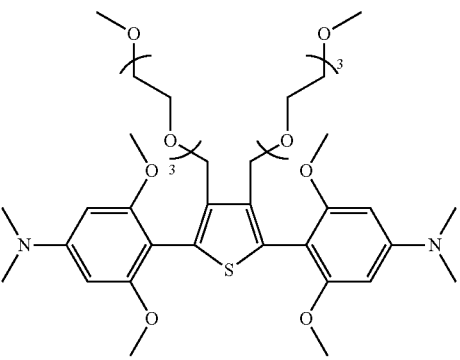
B-8
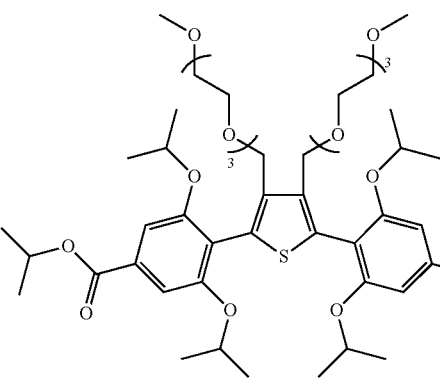
B-9
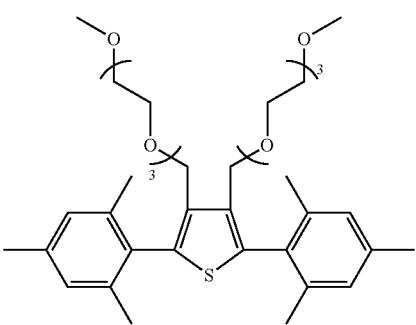
B-10
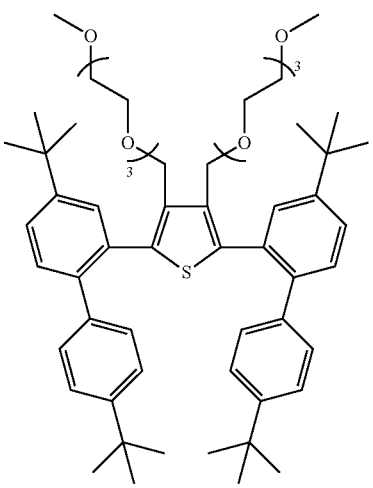

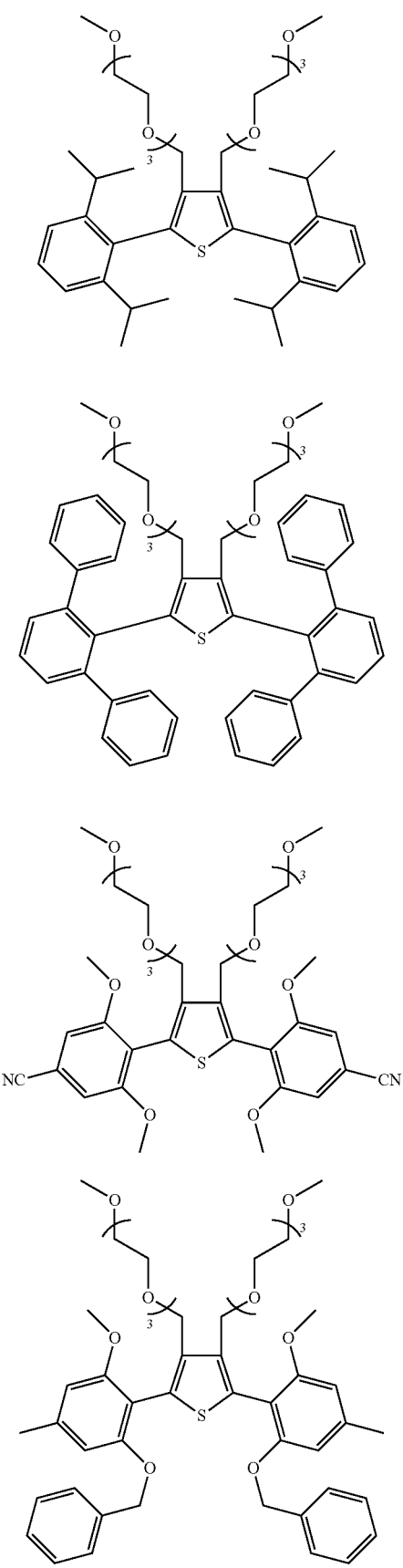
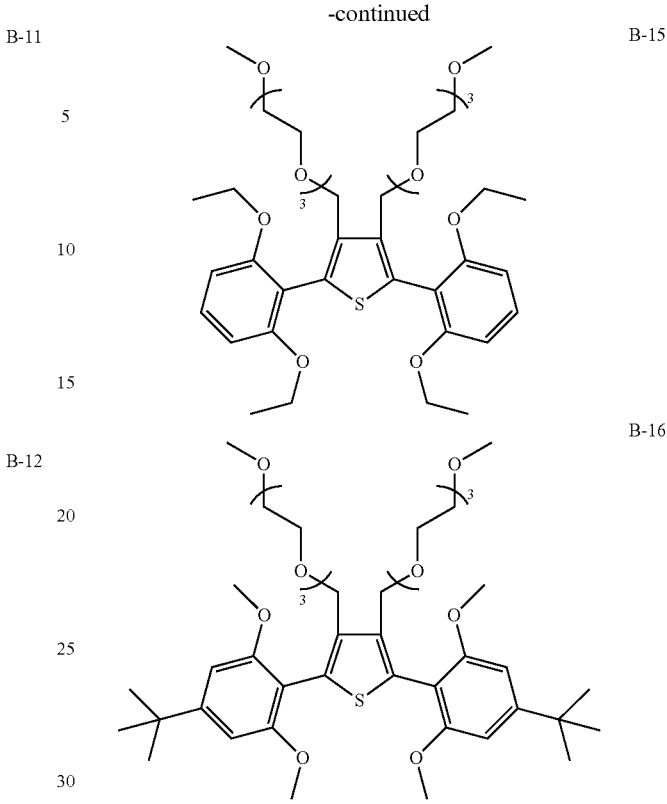

Among the illustrated compounds listed, the compounds belonging to the A group have features shown in the following (ia) to (ic).

(ia) $A_3$ is the same as $A_1$, and $A_4$ is the same as $A_2$. (ib) $A_1$ and $A_2$ each represent a methoxy group or an isopropoxy group. (ic) x represents any one of 1 to 10.

Further, in the compounds belonging to the A group, the sterically-hindered group shown as any one of $A_1$ to $A_4$ is an alkyl group, an alkoxy group or an aryl group.

The illustrated compounds belonging to the B group have features shown in the following (iia) to (iid).

(iia) $A_3$ is the same as $A_1$, and $A_4$ is the same as $A_2$. (iib) $A_1$ and $A_2$ each represent an alkyl group, an alkoxy group or an aryl group.
(iic) $R_1$ represents a hydrogen atom, a halogen atom, an alkyl group having 1 or more and 20 or less carbon atoms, an alkoxy group having 1 or more and 20 or less carbon atoms, an alkyl ester group having 1 or more and 20 or less carbon atoms, an aryl group, an optionally substituted amino group or a cyano group.
(iid) x represents 3.

Further, in all of the illustrated compounds listed, substituents each having an ethylene oxide chain having high compatibility to an organic solvent are introduced into the carbon atoms at the 3-position and the 4-position constituting the thiophene ring which is a light absorbing moiety. Therefore, the illustrated compounds listed have high solubility in an organic solvent (particularly, in a polar solvent). Further, in the illustrated compounds listed, substituents such as an alkoxy group, an alkyl group and an aryl group are substituted at the ortho positions of the benzene ring bonded to the thiophene ring. These substituents play a role of sterically protects the thiophene ring together with ethylene oxide chains, the thiophene ring forming radical cations in the colored state by oxidation.

Therefore, the organic compound of the present invention has high solubility in an organic solvent and high durability against repetition of an oxidation-reduction.

[EC Device]

The organic compound (electrochromic compound, EC organic compound) of the present invention can be used as a component of an electrochromic layer (EC layer) constituting an electrochromic device (EC device).

Figure 2:
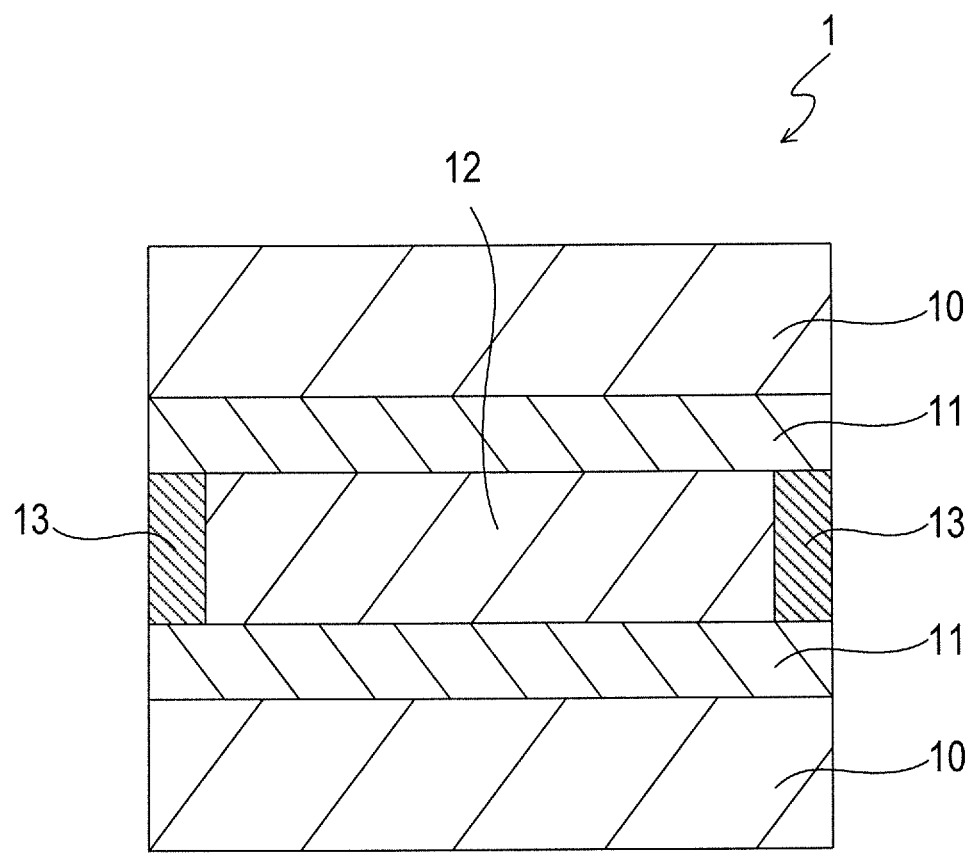
FIG. 2 is a schematic sectional view illustrating an example of the embodiments of the electrochromic device of the present invention.

The EC device according to the present embodiment will be described below with reference to drawings. FIG. 2 is a schematic sectional view illustrating an example of the embodiments of the electrochromic device of the present invention.

The EC device 1 in FIG. 2 has a pair of transparent electrodes 11 and an EC layer 12 arranged between the pair of transparent electrodes 11.

In the EC device 1 in FIG. 2, each transparent electrode 11 is provided on one surface of a substrate 10, and the two substrates 10 constituting the EC device 1 are arranged so that the pair of transparent electrodes 11 are opposed to each other. Further, the transparent electrodes 11 are arranged so that the distance between the electrodes is a predetermined value with a spacer 13.

In the EC device 1 in FIG. 2, the EC layer 12 is a layer containing an electrolyte and the organic compound (EC organic compound) according to the present invention. Examples of the specific structure of the EC layer 12 include the following structures (A) to (C). The structure (C) is preferred.

(A) A layer prepared by mixing an EC organic compound and an electrolyte (B) A laminate including a layer including an EC organic compound and a layer including an electrolyte (C) A layer including a solution containing an EC organic compound and an electrolyte (D) A layer including an EC organic compound, an electrolyte and a matrix of the EC layer 12

Next, the components of the EC device of the present invention will be described.

Examples of the transparent substrate 10 constituting the EC device 1 include colorless or colored glass, tempered glass, and colorless or colored transparent resin. Note that, in the present embodiment, the term "transparent" means that visible light transmittance is 90% or more.

Specific examples of the transparent resin used as the transparent substrate 10 include polyethylene terephthalate, polyethylene naphthalate, polynorbornene, polyamide, polysulfone, polyether sulfone, polyether ether ketone, polyphenylene sulfide, polycarbonate, polyimide and polymethylmethacrylate.

Examples of the electrode material used to form the transparent electrode 11 constituting the EC device 1 include metals and metal oxides such as an indium tin oxide alloy (ITO), fluorine doped tin oxide (FTO), tin oxide (NESA), zinc indium oxide, silver oxide, vanadium oxide, molybdenum oxide, gold, silver, platinum, copper, indium and chromium, silicon-based materials such as polycrystalline silicon and amorphous silicon, and carbon materials such as carbon black, graphite and glassy carbon.

Further, conductive polymers in which electric conductivity is improved by doping treatment or the like, for example, polyaniline, polypyrrole, polythiophene, polyacethylene, poly(para-phenylene) and a complex of polyethylene dioxythiophene (PEDOT) and polystyrene sulfonate are suitably used.

The electrolyte contained in the EC layer 12 constituting the EC device 1 is not limited as long as the electrolyte is an ionic dissociative salt and has good solubility in a solvent. Note that when the electrolyte is a solid, an electrolyte having high compatibility with the organic compound of the present invention is preferred. Further, an electrolyte having electron-donating properties among the electrolytes is preferred. Here, the electrolyte contained in the EC layer 12 can also be referred to as a supporting electrolyte.

Examples of the electrolyte contained in the EC layer 12 include inorganic ionic salts such as various alkali metal salts and alkaline earth metal salts, quaternary ammonium salts and cyclic quaternary ammonium salts.

Specific examples include alkali metal salts of Li, Na and K such as $LiClO_4$, $LiSCN$, $LiBF_4$, $LiAsF_6$, $LiCF_3SO_3$, $LiPF_6$, $LiI$, $NaI$, $NaSCN$, $NaClO_4$, $NaBF_4$, $NaAsF_6$, $KSCN$ and $KCl$, and quaternary ammonium salts and cyclic quaternary ammonium salts such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$ and $(n-C_4H_9)_4NClO_4$.

When the structure of the EC layer 12 is the above (C), the EC layer 12 consists of a liquid material. Further, a solvent which dissolves the organic compound (EC organic compound) of the present invention and an electrolyte may be contained in the EC layer 12. The solvent is not particularly limited as long as the solvent can dissolve the organic compound of the present invention and an electrolyte, but a solvent having polarity is particularly preferred.

Specific examples include water and organic polar solvents such as methanol, ethanol, propylene carbonate, ethylene carbonate, dimethyl sulfoxide, dimethoxyethane, γ-butyrolactone, γ-valerolactone, sulfolane, dimethylformamide, dimethoxyethane, tetrahydrofuran, acetonitrile, propionitrile, 3-methoxy propionitrile, benzonitrile, dimethylacetamide, methylpyrrolidinone and dioxolane.

When the structure of the EC layer 12 is the above (D), examples of the matrix contained in the EC layer 12 include a polymer and a gelling agent. The EC layer 12 becomes a highly viscous member or a gel member by incorporating a gelling agent into the EC layer 12.

In the present invention, the polymer serving as the above matrix is not particularly limited, and examples thereof include polyacrylonitrile, carboxymethyl cellulose, polyvinyl chloride, polyethylene oxide, polypropylene oxide, polyurethane, polyacrylate, polymethacrylate, polyamide, polyacrylamide, polyester and Nafion (registered trademark).

The spacer 13 constituting the EC device 1 is a member for holding the pair of electrodes 11 at a predetermined distance and giving a space for forming the EC layer 12. Specifically, the spacer can be formed using a resin material such as polyimide, polytetrafluoroethylene, fluororubber and an epoxy resin.

When the structure of the EC layer constituting the EC device 1 is the above (C), the device can be produced by forming a liquid inlet (not shown) using the pair of transparent electrodes 11 and the spacer 13, charging a solution-form composition constituting the EC layer 12 from the liquid inlet, covering the inlet with a sealing member, and then sealing the inlet with an adhesive or the like.

The sealing member for sealing the composition constituting the EC layer 12 also bears a role of isolating the adhesive from the EC organic compound so that the adhesive and the compound are not brought into contact with each other. The shape of the sealing member can be, but is not particularly limited to, a tapered shape such as a wedge.

In the present invention, a method for forming an EC device is not particularly limited. Examples of the method that can be used include a method of installing two substrates 10 each having a transparent electrode 11 so that a predetermined gap is formed between the pair of transparent electrodes 11 using a spacer 13 or the like and then injecting a previously prepared liquid composition for the EC layer 12 by a vacuum injection method, an atmospheric air injection method, a meniscus method or the like.

In the EC device of the present invention, other EC compounds may be contained in the EC layer 12 in addition to the organic compound (EC organic compound) of the present invention. The EC compounds other than the organic compound of the present invention which may be contained in the EC layer 12 may be one type or a plurality of types. Further, the EC compound contained in the EC layer 12 may be a compound colored in the oxidized state, may be a compound colored in the reduced state or may be both thereof. Particularly, a compound colored in the reduced state is preferred among them.

The absorption wavelength region of the EC compounds other than the organic compound of the present inventions is preferably 400 nm or less in the bleached state. This is because a device having high transparency in the bleached state can be provided. On the other hand, the absorption wavelength region in the colored state is preferably in the range of 400 nm or more and 800 nm or less, more preferably in the range of 450 nm or more and 700 nm or less.

When EC compounds other than the organic compound of the present invention are contained in the EC layer 12, the compounds can be suitably selected so that the resulting EC device absorbs the light in the visible light region uniformly at each wavelength.

Here, examples of the EC compounds other than the organic compound of the present invention include compounds listed below.

Examples of the EC compounds which are colored in the oxidized state include oligothiophenes, phenazine-based compounds such as 5,10-dihydro-5,10-dimethylphenazine and 5,10-dihydro-5,10-diethylphenazine, metallocene-based compounds such as ferrocene, tetra-t-butylferrocene and titanocene, phenylenediamine-based compounds such as N,N',N,N'-tetramethyl-p-phenylenediamine, and pyrazoline-based compounds such as 1-phenyl-2-pyrazoline.

Examples of the EC compounds which are colored in the reduced state include viologen-based compounds such as N,N'-diheptyl bipyridinium diperchlorate, N,N'-diheptyl bipyridinium ditetrafluoroborate, N,N'-diheptyl bipyridinium dihexafluorophosphate, N,N'-diethyl bipyridinium diperchlorate, N,N'-diethyl bipyridinium ditetrafluoroborate, N,N'-diethyl bipyridinium dihexafluorophosphate, N,N'-dibenzyl bipyridinium diperchlorate, N,N'-dibenzyl bipyridinium ditetrafluoroborate, N,N'-dibenzyl bipyridinium dihexafluorophosphate, N,N'-diphenyl bipyridinium diperchlorate, N,N'-diphenyl bipyridinium ditetrafluoroborate and N,N'-diphenyl bipyridinium dihexafluorophosphate, anthraquinone-based compounds such as 2-ethyl anthraquinone, 2-t-butyl anthraquinone and octamethyl anthraquinone, ferrocenium salt-based compounds such as ferrocenium tetrafluoroborate and ferrocenium hexafluorophosphate, and styryl-based compounds.

The EC device of the present invention has high transparency in the bleached state, and can give high optical density and reduce transmittance in the colored state because the organic compound according to the present invention has high solubility in an organic solvent. Therefore, the EC device can be suitably used when the incident light quantity into an image pickup device such as a camera is significantly reduced.

The EC device of the present inventions can be used as a component of an optical filter, a lens unit, an imaging device and a window material.

The optical filter of the present invention has the EC device of the present invention and an active element to be electrically connected to the EC device. Specific examples of the active element to be electrically connected to the EC device include a switching element for controlling the transmittance of the EC device. Examples of the switching element include TFT and a MIM element. TFT is also referred to as a thin-film transistor, and semiconductors and oxide semiconductors are used as the components thereof. Specific examples include semiconductors in which amorphous silicon, low-temperature polysilicon or InGaZnO is used as a component.

The lens unit of the present inventions has a plurality of lenses and an optical filter having the EC device. The optical filter constituting the lens unit may be provided between the plurality of lenses or may be provided in the outside of the lenses. The optical filter can preferably be provided on the optical axis of the lenses.

The imaging device of the present invention has an optical filter and a photodetection element for receiving light having passed through the optical filter.

Specific examples of the imaging device include a camera, a video camera and a camera-equipped mobile phone. The imaging device may have a form in which a body having a photodetection element and a lens unit having lenses which can be separated.

Here, when the imaging device can be separated into a body and a lens unit, a form in which an optical filter separated from the imaging device is used during imaging is also included in the present invention. Note that, in such a case, examples of the arrangement position of the optical filter include outside the lens unit, between the lens unit and the photodetection element and between a plurality of lenses (when the lens unit has a plurality of lenses).

The window material of the present invention has a pair of transparent substrates, an EC device provided between these transparent substrates and an active element for controlling the transmittance of the EC device. The active element is connected to the EC device, and the connection form to the EC device may be a directly connected form or may be an indirectly connected form. The window material of the present invention can be used for windows of airplanes, motor vehicles, and homes. Further, the window material having the EC device can also be referred to as a window material having an electronic curtain.

Figure 3:
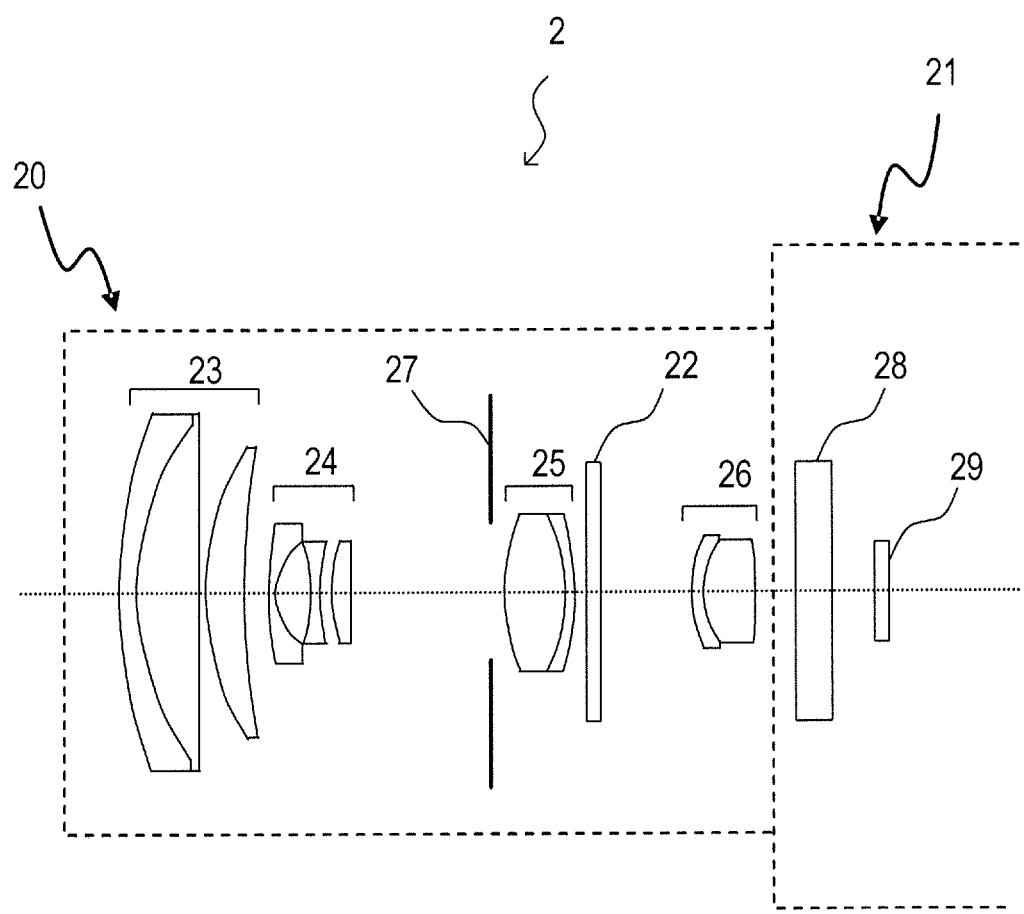
FIG. 3 is a schematic sectional view illustrating a first embodiment of an imaging device having the electrochromic device of the present invention.
Figure 4:
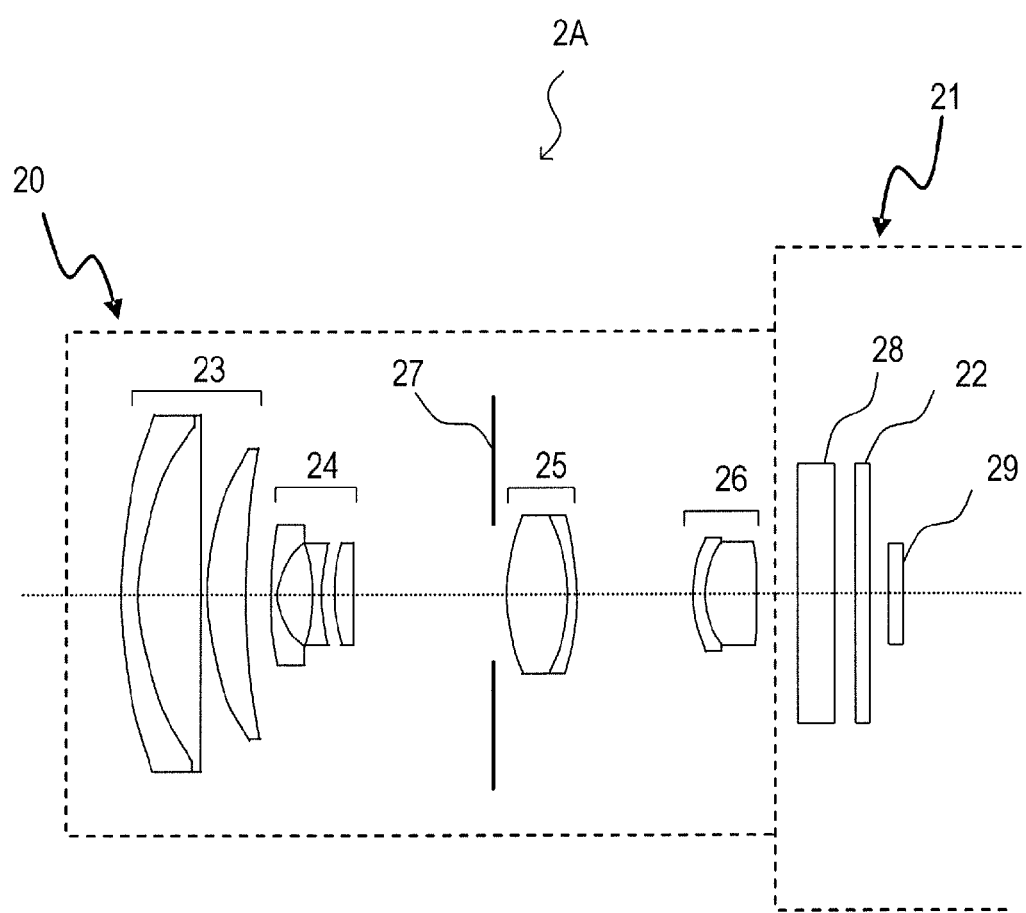
FIG. 4 is a schematic sectional view illustrating a second embodiment of an imaging device having the electrochromic device of the present invention.

Various apparatuses having the EC device of the present invention will be described below with reference to drawings. FIG. 3 is a schematic sectional view illustrating a first embodiment of an imaging device having the electrochromic (EC) device of the present invention. Further, FIG. 4 is a schematic sectional view illustrating a second embodiment of an imaging device having the electrochromic (EC) device of the present invention.

An imaging device 2 of FIG. 3 is an apparatus including a lens unit 20 and an imaging unit 21. Note that the lens unit 20 and the imaging unit 21 are detachably connected through a mount member (not shown).

In the imaging device 2 of FIG. 3, the lens unit 20 is provided with a plurality of lenses, specifically a first lens 23, a second lens 24, a third lens 25 and a fourth lens 26 from the side close to an image (the side far from the imaging unit 21). However, the lenses in the lens unit 20 are not limited to four lenses illustrated as reference numerals 23 to 26 in FIG. 3. Note that, with respect to these lenses (23 to 26), each lens may be composed of a single lens or may be composed of a plurality of lenses as illustrated in FIG. 3.

In the imaging device 2 of FIG. 3, each lens in the lens unit 20, for example, plays a role to be described below. That is, the second lens 24 and the third lens 25 achieve a function of changing magnification by changing the space between the lenses, and the fourth lens 26 achieves a function of focusing by moving the lens.

In the imaging device 2 of FIG. 3, the lens unit is provided with an aperture stop 27, for example, between the second lens 24 and the third lens 25.

Further, the lens unit 20 is provided with an optical filter 22 between the third lens 25 and the fourth lens 26. Note that, the arranging mode of the optical filter 22 is not limited to the mode illustrated in FIG. 3. For example, the arranging mode may be any one of the modes to be shown in the following (1) to (3).

(1) Between the first lens 23 and the second lens 24
(2) Between a glass block 28 and a photodetection element 29 (FIG. 4)
(3) Between the fourth lens 26 and the glass block 28

In the imaging device 2 of FIG. 3, the optical filter 22 has the EC device of the present invention and an active element connected to the EC device.

Here, since the optical filter 22 can exhibit high transparency when the EC device provided in the optical filter 22 is in the bleached state, most of the incident light which is incident on the optical filter 22 is transmitted, and therefore, the transmitted light volume through the optical filter 22 itself will be sufficient. On the other hand, when the EC device is in the colored state, the incident light can be reliably shaded or modulated by the optical filter 22. Further, as already described, the EC device provided in the optical filter 22 is a long-life device because the device is excellent in characteristics against repetition of an oxidation-reduction.

In the imaging device 2 of FIG. 3, the glass block 28 contained in the imaging unit 21 is a glass block such as a low-pass filter, a face plate and a color filter.

In the imaging device 2 of FIG. 3, the photodetection element 29 contained in the imaging unit 21 is a sensor part which receives the light having passed through the lens unit 20, and an image pickup device such as CCD and CMOS can be used for the photodetection element 29. Further, the photodetection element 29 may be a photosensor such as a photodiode, and a photosensor which acquires and outputs information on the intensity or wavelength of light can be suitably utilized.

Figure 5A:
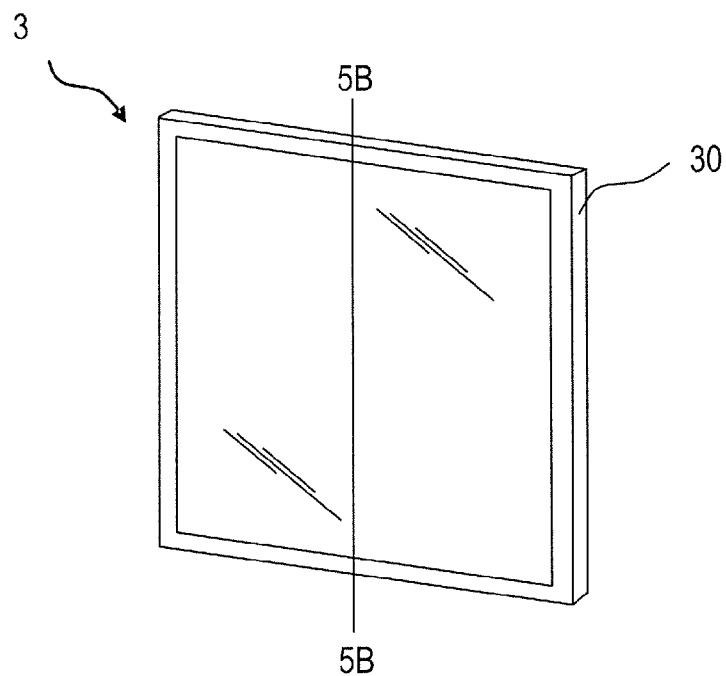
FIG. 5A is a perspective view illustrating an example of a window having the electrochromic device of the present invention.
Figure 5B:
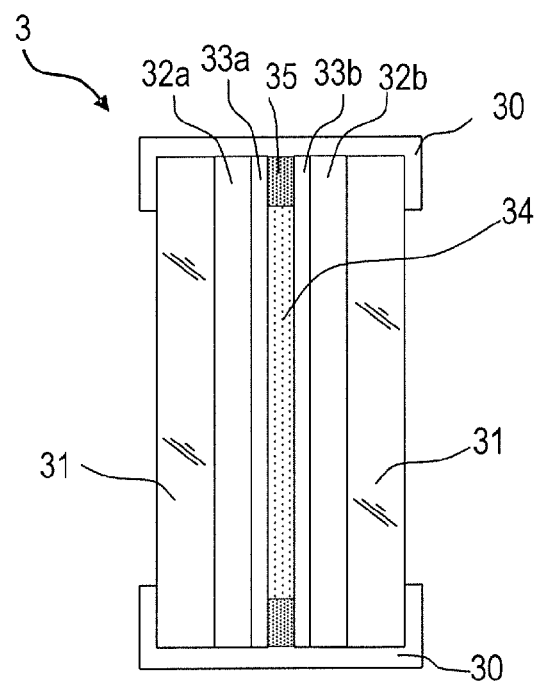
FIG. 5B is a sectional view illustrating the 5B-5B section in FIG. 5A.

FIG. 5A is a perspective view illustrating an example of a window having the electrochromic device of the present invention, and FIG. 5B is a sectional view illustrating the 5B-5B section in FIG. 5A.

A window 3 illustrated in FIG. 5A includes a window frame 30 and a window member fixed to the window frame 30. Note that, in the window 3 illustrated in FIG. 5A, the edge of the window member is fixed to the window frame 30.

In the window 3 of FIG. 5B, a window member is a member including a pair of window plates 31 and an EC device which is provided between the window plates 31 and in which a first substrate 32a, a first electrode 33a, an EC layer 34, a second electrode 33b and a second substrate 32b are provided in this order. Note that, in the EC device, a spacer 35 is provided between the first electrode 33a and the second electrode 33b for the purpose of holding the space between the first electrode 33a and the second electrode 33b and fixing the EC layer 34 between the two electrodes (33a, 33b).

In the window 3 of FIG. 5A, examples of the window plate 31 include a material generally used as a window plate constituting a window, and specific examples thereof include a plate-like member made of glass, a resin having a high light transmittance such as an acrylic resin and the like.

Incidentally, when the EC device provided in the window 3 of FIG. 5A is in the bleached state, the EC device can exhibit high transparency, and therefore, most of the incident light which is incident on the window 3 is transmitted. On the other hand, when the EC device is in the colored state, the EC device can interrupt the incident light which is incident on the window 3 or modulate the color or the like of the incident light. Further, as already described, the EC device provided in the window 3 is a long-life device because the device is excellent in characteristics against repetition of an oxidation-reduction.

EXAMPLES

The present invention will be more specifically described below with reference to Examples, but the present invention is not limited to these Examples.

Example 1

Synthesis of Illustrated Compound A-1

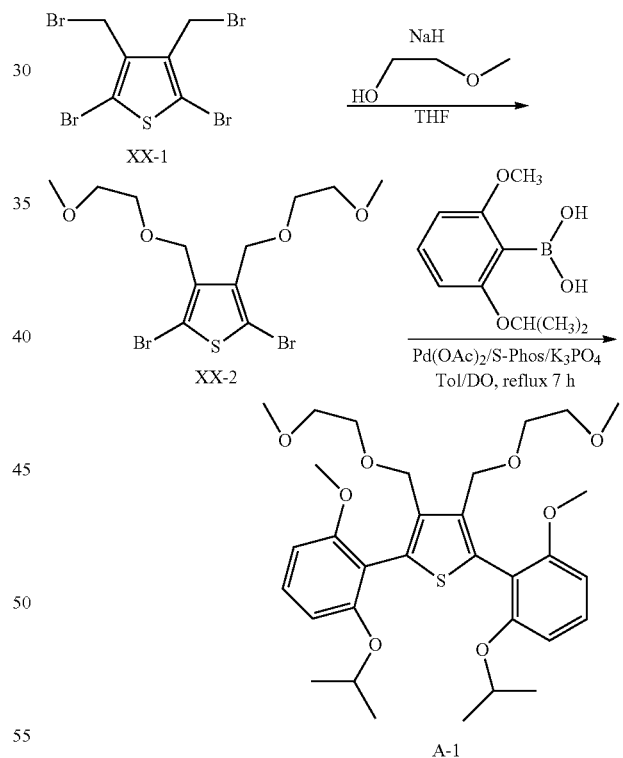

(1) Synthesis of compound XX-2

A reagent and a solvent as shown below were charged to a 50-ml reaction vessel to disperse sodium hydride in the solvent.

Dehydrated tetrahydrofuran: 3 ml
Sodium hydride: 163 mg (60%, 4.09 mmol)

Next, 2-methoxyethanol (311 mg, 4.09 mmol) was added to the above reaction solution, and the mixture was then stirred under nitrogen flow for 30 minutes, thus removing generated hydrogen.

Then, a solution prepared by mixing 2,5-dibromo-3,4-bis(bromomethyl)thiophene (compound XX-1, 700 mg, 1.636 mmol) and dehydrated tetrahydrofuran (4 ml) was dropwisely added to the reaction solution. Note that the compound XX-1 is a compound synthesized from 3,4-dimethylthiophene as a starting material according to the synthetic method described in Journal of the American Chemical Society, 111, 3659 (1989). After that, the reaction solution was further stirred for 5 hours at room temperature to allow the reaction to complete.

Next, water was added to the reaction solution to stop the reaction, and the reaction solution was then subjected to solvent extraction operation using ethyl acetate to obtain an organic layer. Then, the organic layer was dried and vacuum-concentrated to thereby obtain a crude product. Finally, the crude product obtained was separated and purified by silica gel chromatography (developing solvent: hexane/ethyl acetate=1/1) to thereby obtain 510 mg (yield: 74.5%) of a compound XX-2 as a colorless oil.

(2) Synthesis of A-1

A reagent and a solvent as shown below were charged to a 50-ml reaction vessel.

Compound XX-2: 480 mg (1.15 mmol)

2-isopropoxy-6-methoxyphenylboronic acid: 723 mg (3.44 mmol)

Toluene: 5 ml 1,4-dioxane: 5 ml

Next, the reaction solution was stirred while introducing nitrogen into the reaction vessel to thereby remove oxygen dissolved in the reaction solution. Then, reagents as shown below were added to the reaction solution.

Pd(OAc)$_2$: 10.3 mg (0.046 mmol)

2-dicyclohexylphosphino-2',6'-dimethoxybiphenyl (S-Phos): 47.3 mg (0.115 mmol)

Tribasic potassium phosphate: 1.32 g (5.75 mmol)

Next, the reaction solution was heated to 100° C. and then stirred at the temperature (100° C.) for 7 hours.

Then, the reaction solution was cooled to room temperature and then vacuum-concentrated to thereby obtain a crude product. Finally, the crude product was separated and purified by silica gel chromatography (developing solvent: ethyl acetate/chloroform=8/1) to thereby obtain 540 mg (yield: 79.7%) of the illustrated compound A-1 as a colorless solid.

The structure of the compound obtained was verified by nuclear magnetic resonance spectroscopy (NMR) measurement. As a result, the compound obtained was verified as the illustrated compound A-1 because the ratio of the peak integral values was well in agreement with that of the structure of the object compound. The results of the measurement of the NMR spectrum are shown below.

$^1$H-NMR (CDCl$_3$) δ (ppm): 7.24 (t, 2H), 6.61 (d, 2H), 6.58 (d, 2H), 4.52-4.35 (m, 6H), 3.74 (s, 4H), 3.71 (s, 2H), 3.45-3.31 (m, 8H), 3.27 (s, 6H), 1.18 (d, 6H), 1.15 (d, 6H).

Figure 6:
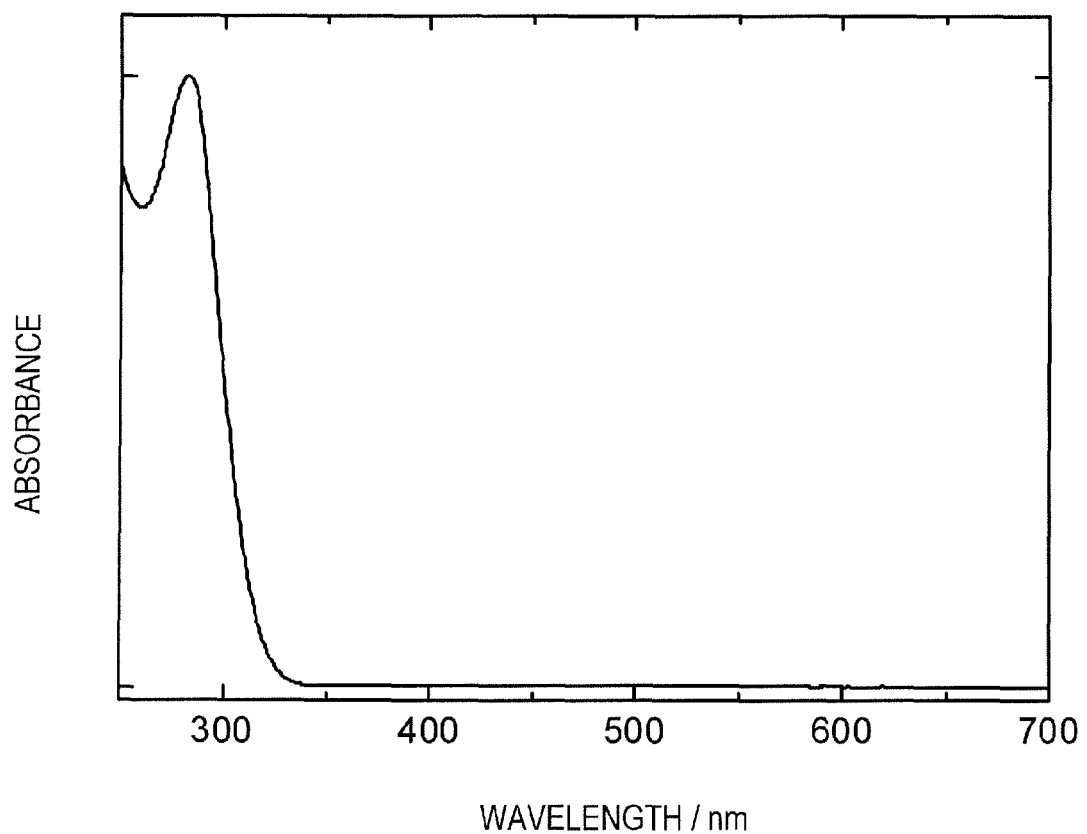
FIG. 6 shows the ultraviolet and visible absorption spectrum of an illustrated compound A-1 in the neutral state.

The illustrated compound A-1 obtained was dissolved in chloroform, and the resulting solution was measured using an ultraviolet and visible spectrophotometer (V-560 manufactured by JASCO Corporation). As a result, an absorption spectrum illustrated in FIG. 6 was obtained. FIG. 6 shows that, in the illustrated compound A-1, the $λ_{max}$ in which the absorption peak has a maximum strength is 282.0 nm in an ultraviolet region. Further, FIG. 6 shows that the illustrated compound A-1 is a transparent material because the compound does not have absorption over the whole visible light region.

Example 2

Synthesis of Illustrated Compound A-3

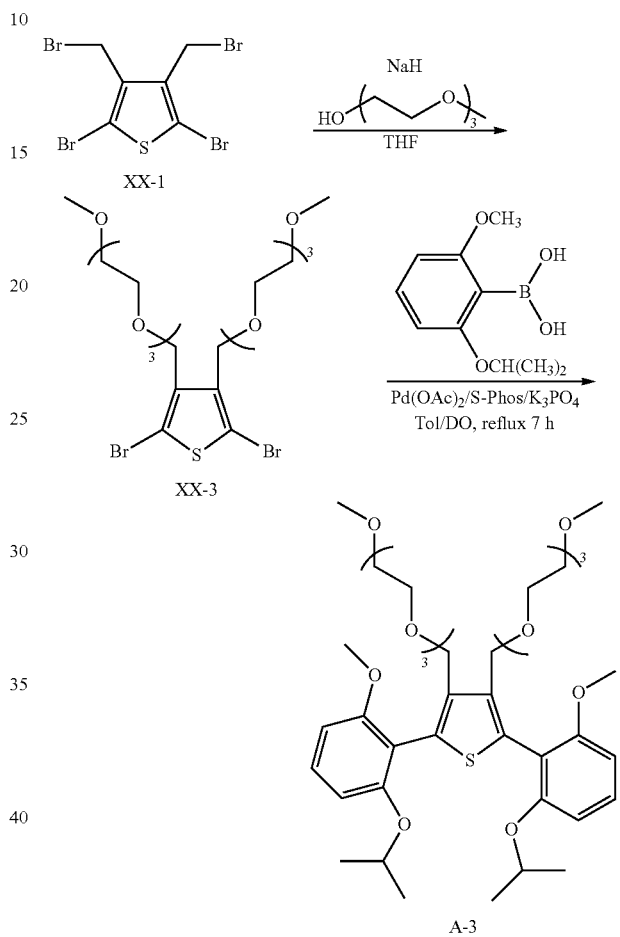

A-3

(1) Synthesis of XX-3

A reagent and a solvent as shown below were charged to a 200-ml reaction vessel to disperse sodium hydride in the solvent.

Dehydrated tetrahydrofuran: 14 ml

Sodium hydride: 300 mg (60%, 7.41 mmol)

Triethylene glycol monomethyl ether (1.22 g, 6.85 mmol) was added to the dispersion, and the reaction solution was then stirred under nitrogen flow for 1 hour, thus removing generated hydrogen.

Next, a solution prepared by mixing 2,5-dibromo-3,4-bis(bromomethyl)thiophene (compound XX-1, 1.44 g, 3.37 mmol) and dehydrated tetrahydrofuran (4 ml) was dropwisely added to the reaction solution, and the resulting mixture was further stirred at room temperature for 3 hours.

Then, water was added to the reaction solution to stop the reaction, and the reaction solution was then subjected to solvent extraction operation using ethyl acetate to obtain an organic layer. After that, the organic layer was dried and vacuum-concentrated to thereby obtain a crude product. Finally, the crude product obtained was separated and purified by silica gel chromatography (developing solvent: ethyl acetate/methanol=20/1) to thereby obtain 1.68 g (yield: 83%) of a compound XX-3 as a light yellow oil.

(2) Synthesis of A-3

A reagent and a solvent as shown below were charged to a 50-ml reaction vessel.

Compound XX-3: 600 mg (1.01 mmol)
2-isopropoxy-6-methoxyphenylboronic acid: 636 mg (3.03 mmol)
Toluene: 5 ml
1,4-dioxane: 5 ml Next, the reaction solution was stirred while introducing nitrogen into the reaction vessel to thereby remove oxygen dissolved in the reaction solution. Then, reagents as shown below were added to the reaction solution.

Pd(OAc)$_2$: 9.0 mg (0.04 mmol)
2-dicyclohexylphosphino-2',6'-dimethoxybiphenyl (S-Phos): 41 mg (0.1 mmol)
Tribasic potassium phosphate: 1.15 g (5.0 mmol)

Next, the reaction solution was heated to 100° C. and then stirred at the temperature (100° C.) for 7 hours.

Then, the reaction solution was cooled to room temperature and then vacuum-concentrated to thereby obtain a crude product. Finally, the crude product was separated and purified by silica gel chromatography (developing solvent: chloroform/acetone=3/2) to thereby obtain 370 mg (yield: 47.9%) of the illustrated compound A-3 as a light yellow solid.

The compound obtained was measured for the NMR spectrum. The results are shown below.

$^1$H-NMR (CDCl$_3$) δ (ppm): 7.24 (t, 2H), 6.60 (d, 2H), 6.57 (d, 2H), 4.54-4.31 (m, 6H), 3.74 (s, 4H), 3.71 (s, 2H), 3.61-3.39 (m, 24H), 3.35 (s, 6H), 1.17 (d, 6H), 1.14 (d, 6H).

The compound obtained (illustrated compound A-3) was dissolved in chloroform, and the resulting solution was measured for an absorption spectrum in the same manner as in Example 1, and as a result, the $\lambda_{max}$ in which the absorption peak has a maximum strength was 282.0 nm in an ultraviolet region. That is, the illustrated compound A-3 is a transparent material because the compound does not have absorption over the whole visible light region.

The synthesis techniques as described above in Examples 1 and 2 are techniques which can be employed even when substituents (A$_1$ to A$_4$, R$_1$) on the phenyl group constituting the compound or the number (x) of repeating units of ethylene oxide chains substituted at the 3-position and the 4-position of the thiophene ring are suitably changed. Therefore, the desired EC organic compounds according to the present invention can be synthesized by the synthesis techniques as described in Examples 1 and 2.

[Measurement of Solubility in Propylene Carbonate]

The illustrated compound A-1 obtained in Example 1, the illustrated compound A-3 obtained in Example 2 and Ref-1 as shown below were each measured for the solubility in propylene carbonate. The results are shown in Table 1.

Ref-1

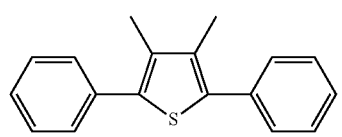

Note that propylene carbonate is a solvent contained in the electrochromic layer constituting the EC device. Further, Ref-1 is a compound in which methyl groups having no ethylene oxide chains are substituted at the 3-position and the 4-position of the thiophene ring, and substituents (substituents corresponding to A$_1$ and A$_2$ in general formula [1]) at the ortho positions of the phenyl group bonded to the thiophene ring are hydrogen atoms (no substitution).

TABLE 1

| Compound | Solubility |
| --- | --- |
| A-1 | 150 mM or more |
| A-3 | 200 mM or more |
| Ref-1 | Less than 6 mM |

Table 1 shows that the illustrated compounds A-1 and A-3 have a high solubility in propylene carbonate. On the other hand, Ref-1 had a low solubility in propylene carbonate, and when a solution having a concentration of 6 mM was going to be prepared, the solution was observed to be turbid. These results showed that the illustrated compounds A-1 and A-3 having ethylene oxide chains as substituents were each found to be a compound that is easily dissolved in propylene carbonate as a solvent.

[Durable Stability Against Oxidation-Reduction Cycle]

The durable stability against the oxidation-reduction cycle of the organic EC compound according to the present invention was evaluated. Specifically, the durability against repetition of an oxidation-reduction was evaluated using the illustrated compound A-1, the illustrated compound A-3 and Ref-1 as evaluation targets.

The measurement of durability against repetition of an oxidation-reduction was performed using a solution prepared by dissolving each compound in a predetermined solvent as a target sample, using a measuring apparatus provided with a work electrode, a counter electrode and a reference electrode. Here, the electrodes provided in the measuring apparatus and the solvent used will be shown below.

Work electrode: Glassy carbon
Counter electrode: Platinum
Reference electrode: Silver
Supporting electrolyte (solvent): Solution of tetrabutylammonium perchlorate in dichloroethane (0.1 mol/L)
Solution concentration: $1.0 \times 10^{-4}$ mol/L The above solution was subjected to a square-wave potential program including oxidation at a constant potential and reduction at a constant potential for 10000 times. Here, the oxidation at a constant potential is a process of applying a potential equal to or higher than the oxidation potential of a target compound to the above solution for 10 seconds, and the reduction at a constant potential is a process of applying a potential of 0 V based on the reference electrode (Ag/Ag$^+$) to the above solution for 10 seconds.

The durability against repetition of an oxidation-reduction was evaluated based on the change in the amount of oxidation peak current in cyclic voltammetry (CV) measurement before and after the oxidation-reduction cycles for 10000 times. Specifically, when the rate of change in the amount of oxidation peak current was less than 20%, the durability was evaluated as Good, and when the rate of change was 20% or more, the durability was evaluated as Poor. The results are shown in Table 2.

TABLE 2

| | Durability evaluation |
| --- | --- |
| Illustrated compound A-1 | Good |
| Illustrated compound A-3 | Good |
| Ref-1 | Poor |

Table 2 shows that, as a result of repeating the oxidation-reduction cycles, the durable stability against the oxidation-reduction cycle of the compound (Ref-1) which is the comparative target of the organic compound of the present invention is poorer than that of the organic compounds (illustrated compounds A-1 and A-3) of the present invention. Specifically, in the case of Ref-1, the amount of oxidation peak current was decreased by 20% after about 2400 times of the oxidation-reduction cycles, suggesting deterioration. On the other hand, in the organic compound (illustrated compounds A-1 and A-3) of the present invention, the change in the amount of oxidation current was less than 20% even after 10000 times of the oxidation-reduction cycles, hence showing stable oxidation-reduction cycles. Therefore, the organic compound according to the present invention is excellent compared with the compound (Ref-1) which is the comparative target in view of the durable stability against the oxidation-reduction cycle.

This is because bulky substituents at the terminal moieties and ethylene oxide chains substituted at the 3-position and the 4-position of thiophene sterically protect the core moiety which generates an unstable radical in the oxidized state. At the same time, the phenyl groups at the terminal moieties are substituted by electron-donating alkoxy groups, which suppress side reaction and deterioration reaction of the core moiety (radical cation) that is electron deficient in the oxidized state, resulting in enhancement of durable stability.

[Evaluation of Electrochromic Characteristics]

Solutions prepared by dissolving compounds synthesized in Examples in chloroform were measured for the absorption spectra in the neutral state (bleached state) using an ultraviolet and visible spectrophotometer (V-560 manufactured by JASCO Corporation).

Next, the absorption spectra in the oxidized (colored) state were measured. Specifically, the absorption spectra were measured using a measuring cell provided with a work electrode, a counter electrode, a reference electrode and a liquid tank. Here, the electrodes provided in the measuring cell and the solute and solvent which are contained in the solution charged to the liquid tank will be shown below.

Work Electrode: Platinum
Counter electrode: Platinum
Reference electrode: Silver
Solute: Evaluation target compounds (illustrated compounds A-1 and A-3)
Solvent (supporting electrolyte): Solution of tetrabutylammonium perchlorate in propylene carbonate (0.1 mol/L)
(Note that the concentration of the solution charged to the liquid tank is $5.0 \times 10^{-4}$ mol/L.)

A compound was subjected to oxidation at a constant potential by applying a potential equal to or higher than the oxidation potential of the compound using the measuring cell to thereby measure the change in the absorption spectra and transmittance spectra. Here, the absorption peak wavelength in the colored state (oxidized state) and the absorption peak wavelength in the bleached state (neutral state) are shown in the following Table 3.

TABLE 3

|  | Neutral absorption $\lambda_{max}$ [nm] | Oxidized absorption $\lambda_{max}'$ [nm] |
| --- | --- | --- |
| Illustrated compound A-1 | 282.0 | 415.8 |
| Illustrated compound A-3 | 282.0 | 419.1 |

Table 3 shows that the compounds synthesized in Examples are transparent materials because all the compounds in the neutral state have an absorption peak wavelength ($\lambda_{max}$) in an ultraviolet region and no absorption over the whole visible light region. Further, Table 3 shows that the compounds synthesized in Examples are visually yellow-colored in the oxidized state because when oxidized, the compounds have absorption in a long wavelength zone of the visible region. Note that since the colored state by oxidation was again returned to a colorless and transparent state by reduction, it was verified that the compounds synthesized in Examples had electrochromic characteristics accompanying oxidation-reduction.

Example 3

Preparation of Electrochromic Device by Use of the Illustrated Compound A-1 and Evaluation Thereof The illustrated compound A-1 prepared in Example 1 and a EC compound C-1 shown below which is colored in the reduced state are dissolved in propylene carbonate to obtain a EC medium, and the concentration of the both compounds in the obtained solution are 75.0 mM, respectively.

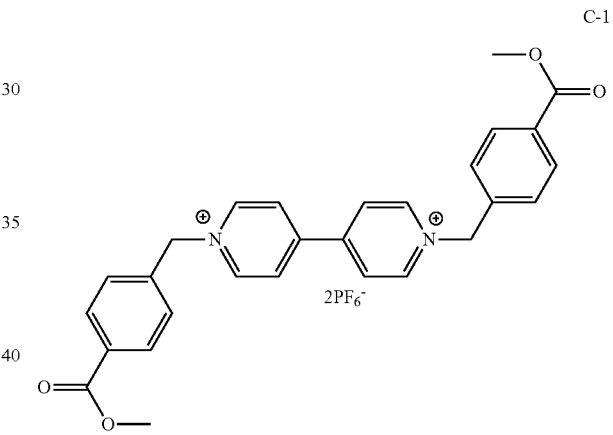

Subsequently, insulating layer ($SiO_2$) was formed on peripheral parts of glass substrate having a transparent conductive film (FTO) (bottom electrode) such that an opening which defined a colored and bleached area remains. Then, Pet film (Melinex(R)S manufactured by Teijin DuPont Films) having a thickness of 50 μm which regulated a distance of the substrate are sandwiched by a glass substrate having a transparent electrode film (upper electrode). After that, an empty cell was prepared by sealing the peripheral parts of a device with an epoxy adhesive so that an opening from which the EC medium was injected remains.

Finally, the EC medium was subjected to the cell from the opening with a vacuum injection method, and then the opening was sealed with the epoxy adhesive to obtain the EC device in the same manner as the peripheral parts.

The EC device has a high transparency and a transmittance of around 80% over the whole range of the visible light region immediately after manufacture of the device.

Figure 7:
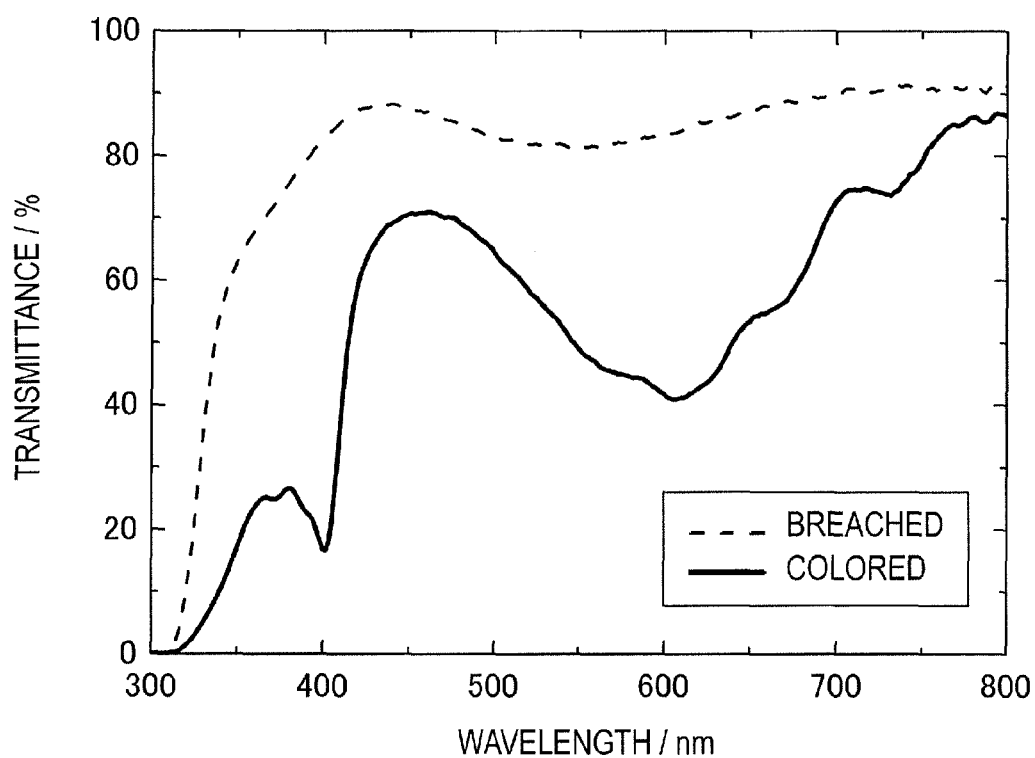
FIG. 7 shows the spectrum of the changes of the transmittance of the EC device before and after applying voltage to the device.

FIG. 7 shows a spectrum of the changes of the transmittance of the EC device before and after applying voltage. Before applying a voltage, the EC device has a transmittance of around 80% indicated by the dashed line. When 2 volt voltage was applied to the EC device, the device was colored and had two main optical absorptions around 415 nm due to an oxidized species of the illustrated compound A-1 and around 605 nm due to a reduced species of the compound C1 which is colored in the reduced state indicated by the solid line. Further, the EC device was bleached by applying of 0 volt voltage, hence showing reversible coloring and bleaching.

Thus, the EC device using the illustrated compound A-1 prepared in Example 1 is confirmed to show an electrochromic characteristic having a large optical density difference between the colored state and the bleached state according to the oxidation and reduction of the compound A-1.

As described above, the organic compound of the present invention has high transparency because the compound does not show light absorption in the visible light region in the bleached state, and has high solubility in an organic solvent. Further, when the compound is used for the EC layer of an EC device, the compound gives high optical density in the colored state, thus the compound is capable of reducing the visible light transmittance of the device.

The organic compound according to the present invention has high transparency because the compound does not have light absorption in the visible light region in the bleached state and has high solubility in an organic solvent, while when oxidized, the compound is colored and can give low transmittance. Therefore, the compound can be utilized for an EC device and a device including the EC device, specifically an optical filter, a lens unit, an imaging device and the like.

The present invention can provide an organic compound having high solubility in a polar solvent used in an EC device, high transparency in the bleached state and high stability against repetition of an oxidation-reduction reaction.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-024330, filed Feb. 12, 2014, and Japanese Patent Application No. 2015-018345, filed Feb. 2, 2015 which are hereby incorporated by reference herein in their entirety.

What is claimed is:

1. An organic compound represented by the following general formula [1]:

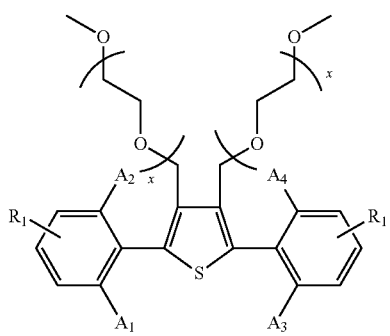

wherein $A_1$ to $A_4$ each represent a substituent selected from the group consisting of a hydrogen atom, an alkyl group having 1 or more and 20 or less carbon atoms, an alkoxy group having 1 or more and 20 or less carbon atoms and an aryl group, provided that at least one of $A_1$ to $A_4$ is an alkyl group, an alkoxy group or an aryl group, wherein when any one of $A_1$ to $A_4$ is an aryl group, the aryl group may further have an alkyl group having 1 or more and 8 or less carbon atoms or an alkoxy group having 1 or more and 8 or less carbon atoms;

$R_1$ represents a hydrogen atom, a halogen atom, an alkyl group having 1 or more and 20 or less carbon atoms, an alkoxy group having 1 or more and 20 or less carbon atoms, an alkyl ester group having 1 or more and 20 or less carbon atoms, an aryl group, an optionally substituted amino group or a cyano group, wherein when $R_1$ is an aryl group, the aryl group may further have an alkyl group having 1 or more and 4 or less carbon atoms; and X is an integer of 1 to 10.

2. The organic compound according to claim 1, wherein the $A_3$ is the same substituent as the $A_1$, and the $A_4$ is the same substituent as the $A_2$.

3. The organic compound according to claim 1, wherein at least one of the $A_1$ to the $A_4$ is an alkoxy group having 1 or more and 20 or less carbon atoms.

4. The organic compound according to claim 3, wherein the alkoxy group is a methoxy group or an isopropoxy group.

5. The organic compound according to claim 1, wherein the X is an integer of 1 or more and 5 or less.

6. An electrochromic device comprising:
a pair of electrodes; and
an electrochromic layer arranged between the pair of electrodes,
wherein the electrochromic layer contains an electrochromic compound and an electrolyte, and the electrochromic compound is an organic compound according to claim 1.

7. The electrochromic device according to claim 6, wherein the electrochromic layer is a layer comprising a liquid material containing the electrochromic compound and the electrolyte.

8. The electrochromic device according to claim 6, wherein the electrochromic layer further contains a second electrochromic compound which is a material other than the organic compound.

9. The electrochromic device according to claim 8, wherein the second electrochromic compound is a compound having low visible light transmittance in the reduced state.

10. An optical filter comprising an electrochromic device according to claim 6 and an active element connected to the electrochromic device.

11. A lens unit comprising a plurality of lenses and an optical filter according to claim 10.

12. An imaging device comprising an optical filter according to claim 10 and a photodetection element for receiving light having passed through the optical filter.

13. A window material comprising a pair of transparent substrates, an electrochromic device according to claim 6 arranged between a pair of the substrates, and an active element connected to the electrochromic device.

* * * * *